(12) United States Patent
Stearns

(10) Patent No.: US 8,450,693 B2
(45) Date of Patent: May 28, 2013

(54) METHOD AND SYSTEM FOR FAULT-TOLERANT RECONSTRUCTION OF IMAGES

(75) Inventor: Charles William Stearns, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 735 days.

(21) Appl. No.: 12/635,877

(22) Filed: Dec. 11, 2009

(65) Prior Publication Data
US 2011/0142304 A1    Jun. 16, 2011

(51) Int. Cl.
*G01T 1/163* (2006.01)
*A61B 6/03* (2006.01)
*H05G 1/64* (2006.01)

(52) U.S. Cl.
USPC ............... 250/363.03; 250/363.04; 378/19; 378/901

(58) Field of Classification Search
USPC ............ 250/363.02–363.04, 370.09; 378/19, 378/98.8
See application file for complete search history.

(56) References Cited

U.S. PATENT DOCUMENTS

| | | | | |
|---|---|---|---|---|
| 5,241,181 A | * | 8/1993 | Mertens et al. | 250/363.03 |
| 5,793,045 A | * | 8/1998 | DiFilippo et al. | 250/363.03 |
| 6,008,493 A | * | 12/1999 | Shao et al. | 250/363.04 |
| 6,403,960 B1 | * | 6/2002 | Wellnitz et al. | 250/363.09 |
| 6,603,125 B1 | * | 8/2003 | Cooke et al. | 250/369 |
| 7,132,663 B2 | * | 11/2006 | Williams et al. | 250/363.03 |
| 7,173,248 B2 | | 2/2007 | Ross et al. | |
| 7,180,055 B1 | * | 2/2007 | Kallenbach et al. | 250/252.1 |
| 7,227,149 B2 | * | 6/2007 | Stearns et al. | 250/363.03 |
| 7,268,354 B2 | * | 9/2007 | Heismann et al. | 250/395 |
| 7,381,959 B2 | | 6/2008 | Manjeshwar et al. | |
| 7,405,405 B2 | * | 7/2008 | Stearns et al. | 250/363.03 |
| 7,447,345 B2 | * | 11/2008 | Shanmugam et al. | 382/131 |
| 7,498,581 B2 | | 3/2009 | Wang et al. | |
| 7,558,414 B2 | | 7/2009 | Griswold | |
| 7,966,155 B2 | * | 6/2011 | Warburton et al. | 702/190 |
| 8,017,914 B2 | * | 9/2011 | Wollenweber et al. | 250/363.04 |
| 2008/0063247 A1 | | 3/2008 | Griswold | |
| 2008/0118020 A1 | | 5/2008 | Thibault et al. | |
| 2008/0240335 A1 | | 10/2008 | Manjeshwar et al. | |

OTHER PUBLICATIONS

Nicholas Tsoulfanidis, Measurement and Detection of Radiation (Washington DC: Taylor & Francis, 1995), p. 73-78.*

* cited by examiner

*Primary Examiner* — Allen C. Ho
(74) *Attorney, Agent, or Firm* — The Small Patent Law Group; Dean D. Small

(57) ABSTRACT

A method and system for reconstructing an image of an object. The method includes acquiring an image dataset of an object of interest, identifying valid data and invalid data in the image dataset, determining a time period that includes the valid data, weighting the valid data based on the determined time period, and reconstructing an image of the object using the weighted valid data.

20 Claims, 7 Drawing Sheets

METHOD AND SYSTEM FOR FAULT-TOLERANT RECONSTRUCTION OF IMAGES

BACKGROUND OF THE INVENTION

The subject matter disclosed herein relates generally to imaging systems, and more particularly, embodiments relate to systems and methods for reconstructing medical images.

Various techniques or modalities may be used for medical imaging of, for example, portions of a patient's body. Positron Emission Tomography (PET) imaging is a non-invasive nuclear imaging technique that makes possible the study of the internal organs of a human body. PET imaging allows the physician to view the patient's entire body, producing images of many functions of the human body.

During operation of a PET imaging system, a patient is initially injected with a radiopharmaceutical that emits positrons as the radiopharmaceutical decays. The emitted positrons travel a relatively short distance before the positrons encounter an electron, at which point an annihilation event occurs whereby the electron and positron are annihilated and converted into two gamma photons each having an energy of 511 keV.

The number of coincidence events per second registered is commonly referred to as prompt coincidences or prompts. Prompts may include true, random, and scatter coincidence events. The data collected during a scan, however, may contain inconsistencies. These inconsistencies may arise from, for example, a transient interruption of communication between the detector and other portions of the imaging system. For example, a transient failure of a detector may cause a temporary loss of imaging data. The collected data is therefore corrected to account for the inconsistencies prior to using such data for reconstruction of the image.

One conventional method of correcting the collected data includes monitoring the performance of the detectors during the scan to determine if the detectors are functioning properly. If a failed detector is identified, the conventional method invalidates the data received from the failed detector over the duration of the scanning procedure. However, the failure of the detector may be transient in nature. For example, the imaging system may experience a temporary communication loss from the detector. In this case, the conventional method still invalidates the data received from the failed detector for the entire scan even though the detector may be generating valid data during a portion of the scan. As a result, the conventional method may reduce the quantity of valid data that is available to reconstruct an image. The reduction in valid data results in a reconstructed image that may have a reduced image quality compared to an image that is reconstructed using the entire set of valid data.

BRIEF DESCRIPTION OF THE INVENTION

In one embodiment, a method for reconstructing an image of an object is provided. The method includes acquiring an image dataset of an object of interest, identifying valid data and invalid data in the image dataset, determining a time period that includes the valid data, weighting the valid data based on the determined time period, and reconstructing an image of the object using the weighted valid data.

In another embodiment, a medical imaging system is provided. The medical imaging system includes a detector and an image reconstruction module coupled to the detector. The image reconstruction module is programmed to receive an image dataset of an object of interest, identify valid data and invalid data in the image dataset, determine a fractional time a detector experienced a transient failure based on the invalid data, weight the valid data based on the fractional time, and reconstruct an image of the object using the weighted valid data.

In a further embodiment, a computer readable medium encoded with a program is provided. The program instructs a computer to receive an image dataset of an object of interest, identify valid data and invalid data in the image dataset, determine a fractional time a detector experienced a transient failure based on the invalid data, weight the valid data based on the fractional time, and reconstruct an image of the object using the weighted valid data.

DETAILED DESCRIPTION OF THE INVENTION

Figure 1:
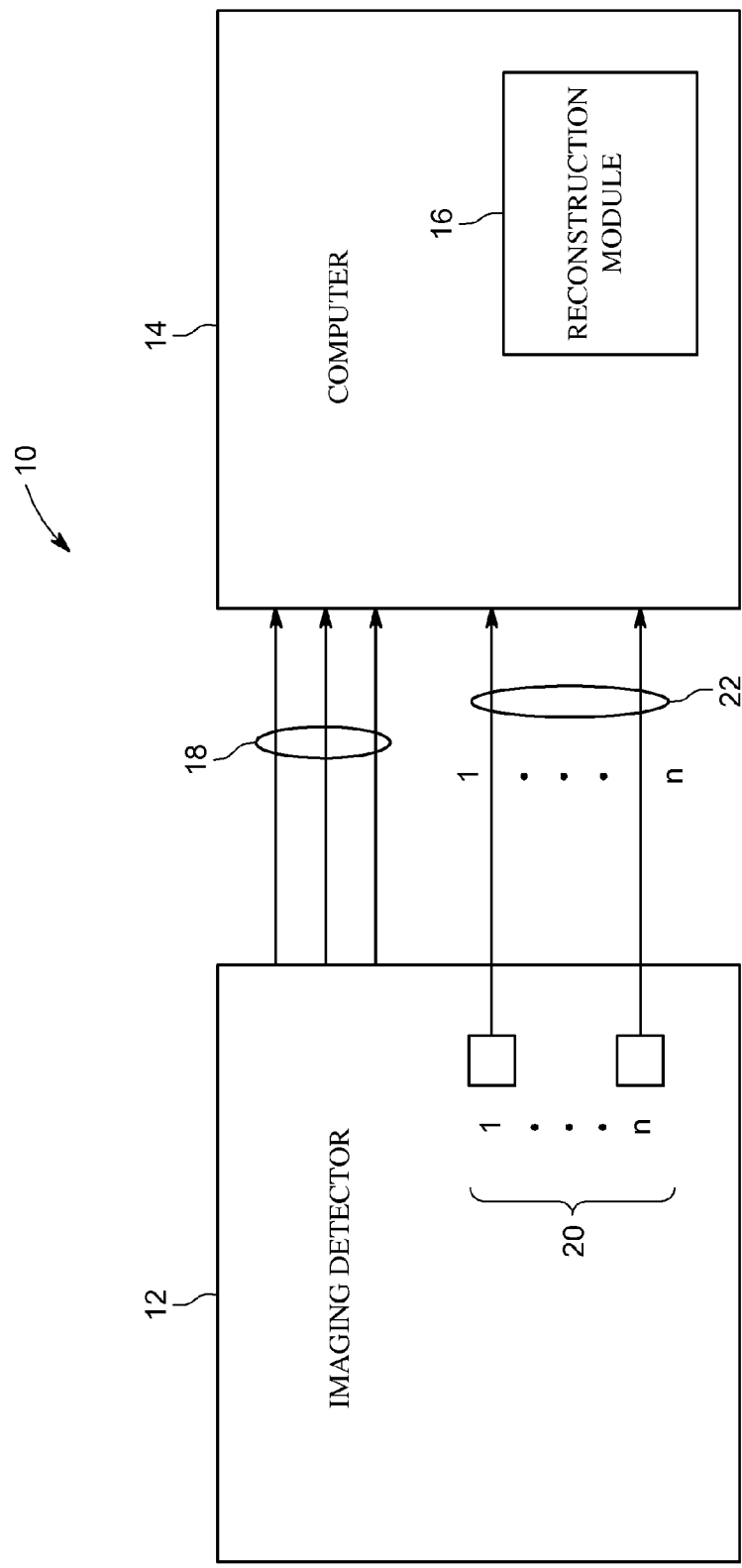
FIG. 1 is a simplified block diagram of an exemplary imaging system formed in accordance with various embodiments of the present invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated, but a viewable image is not. Therefore, as used herein the term "image" broadly refers to both viewable images and data representing a viewable image. However, many embodiments generate, or are configured to generate, at least one viewable image.

FIG. 1 is a schematic block diagram of an exemplary imaging system 10 formed in accordance with various embodiments described herein. In the exemplary embodiments, the imaging system 10 is a Nuclear Medicine (NM) imaging system, for example a Positron Emission Tomography (PET) imaging system. Optionally, the imaging system 10 may be a Single Photon Emission Computed Tomography (SPECT) imaging system.

The imaging system 10 includes a detector 12 that is utilized to scan an object or patient. The imaging system 10 also includes a computer 14 and an image reconstruction module 16. As used herein, the term "computer" may include any processor-based or microprocessor-based system including systems using microcontrollers, reduced instruction set computers (RISC), application specific integrated circuits (ASICs), field programmable gate array (FPGAs), logic circuits, and any other circuit or processor capable of executing the functions described herein. The above examples are exemplary only, and are thus not intended to limit in any way the definition and/or meaning of the term "computer". In the exemplary embodiment, the computer 14 executes a set of instructions that are stored in one or more storage elements or memories, in order to process input data. The storage elements may also store data or other information as desired or needed. The storage element may be in the form of an information source or a physical memory element within the computer 14. The computer 14 may be implemented as an operator workstation that is utilized to control the operation of the imaging system 10. Optionally, the computer 14 may be formed as part of an operator workstation. In a further embodiment, the computer 14 may be a separate component that communicates with the operator workstation.

In the exemplary embodiment, the image reconstruction module 16 is implemented as a set of instructions on the computer 14. The set of instructions may include various commands that instruct the computer 14 to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

Referring again to FIG. 1, the imaging system 10 also includes a communication link 18 that connects or communicates information from the detector 12 to the computer 14. The information may include, for example, emission data generated by a plurality of detector elements 20 during a medical scanning procedure. The imaging system 10 also includes at least one communication link 22 that connects the detector 12 to the computer 14 and/or the image reconstruction module 16. In one exemplary embodiment, the imaging system 10 includes n detector elements 20 and n communication links 22. Optionally, the imaging system 10 includes n detector elements 20 and fewer communication links that transmit a plurality of detector busy signals to the computer 14. For example, the imaging system 10 may include a single communication link 22 that transmits a plurality of detector busy signals to the computer 14.

During operation, the output from the detector 12, referred to herein as an image data set or raw image data, is transmitted to the image reconstruction module 16 via the communication link 18. The image reconstruction module 16 is configured to utilize the image data set to identify and remove invalid data to form an image data subset. The image data subset is then used to reconstruct an image data subset. Moreover, the communication link(s) 22 are configured to transmit a "detector busy signal" from each respective detector element 20 to the computer 14 and/or the image reconstruction module 16. A detector busy signal as used herein refers to a physical signal that indicates that a detector element is currently counting an event to determine if the event falls within a predetermined window. The predetermined window is configured to enable the computer to identify a true event, a random event, and/or a scatter event.

For example, annihilation events are typically identified by a time coincidence between the detection of the two gamma photons in the two oppositely disposed detectors such that the gamma photon emissions are detected virtually simultaneously by each detector. More specifically, during an annihilation event, the electron and positron are converted into two gamma photons each having an energy of 511 keV. Annihilation events are typically identified by a time coincidence between the detection of the two 511 keV gamma photons in the two oppositely disposed detectors, i.e., the gamma photon emissions are detected virtually simultaneously by each detector. When two oppositely traveling gamma photons each strike an oppositely disposed detector to produce a time coincidence, gamma photons also identify a line of response, or LOR, along which the annihilation event has occurred.

However, during an image acquisition process, or in a post-processing step, inconsistencies in the data used to reconstruct an image may arise from, for example, a transient failure of a portion of the imaging system 10. Such transient failures may include, for example, a transient failure of a detector element, a transient failure of communication between the detector element and another portion of the imaging system 10, or a transient failure of the computer 14, for example. Accordingly, the image reconstruction module 16 is configured to utilize the detector busy signal to statistically analyze the image data to identify variations in the image data that are indicative of a transient failure of a detector element 20. At least some of the valid portions of the image data, that is image data acquired when the detector 12 was not experiencing a transient failure, may then be weighted to reconstruct an image of the object.

Figure 2:
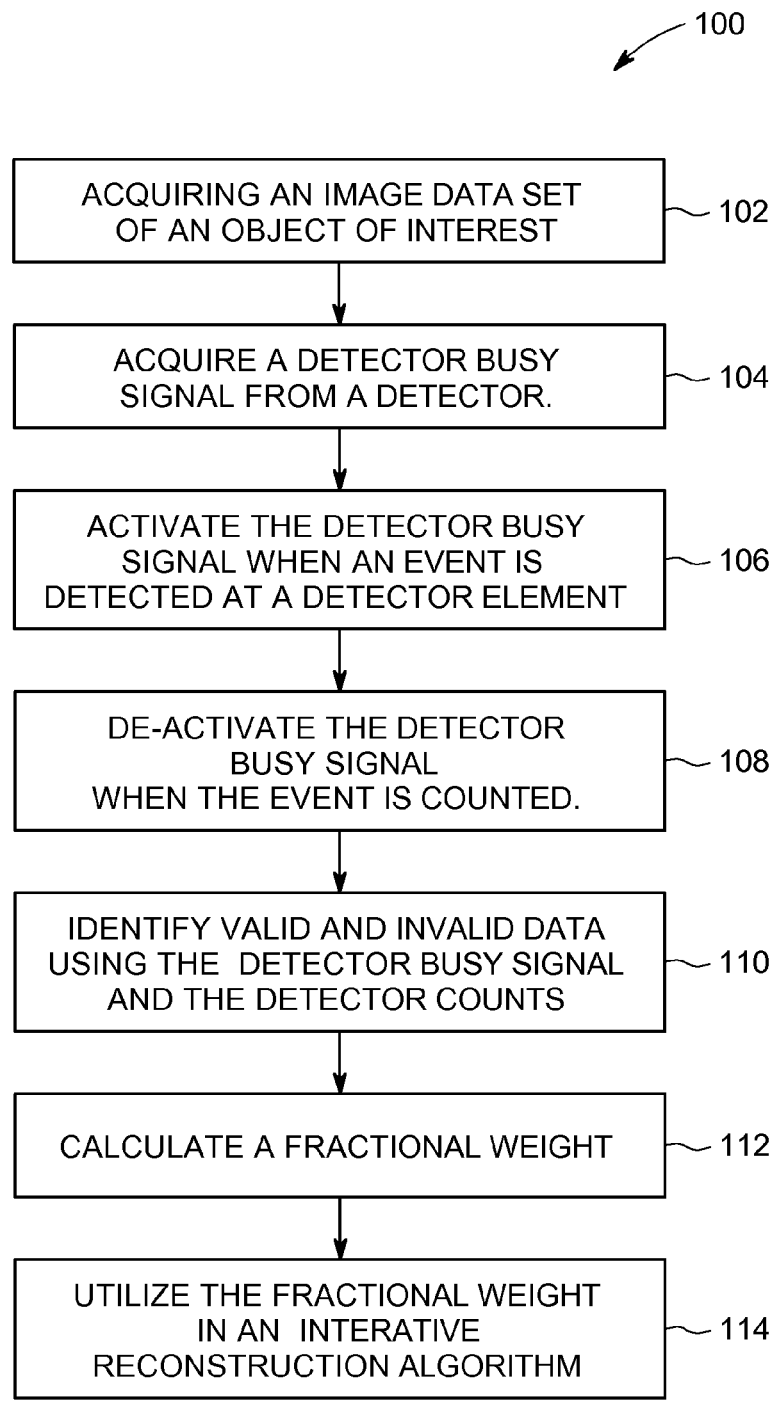
FIG. 2 is a flowchart of an exemplary method for reconstructing an image in accordance with various embodiments of the present invention.

For example, FIG. 2 is a block diagram of an exemplary method 100 of reconstructing an image. The method 100 may be performed by the image reconstruction module 16 shown in FIG. 1. The method 100 includes acquiring 102 an image dataset of an object of interest. In one embodiment, the image dataset may be acquired by scanning a patient using an imaging system. In the exemplary embodiment, the patient is scanned using a medical imaging system, such as a Nuclear Medicine (NM) imaging system, for example the PET or SPECT imaging system described above. The information acquired during the scanning procedure is then stored as listmode data in the imaging system 10, or a remote location.

Figure 3:
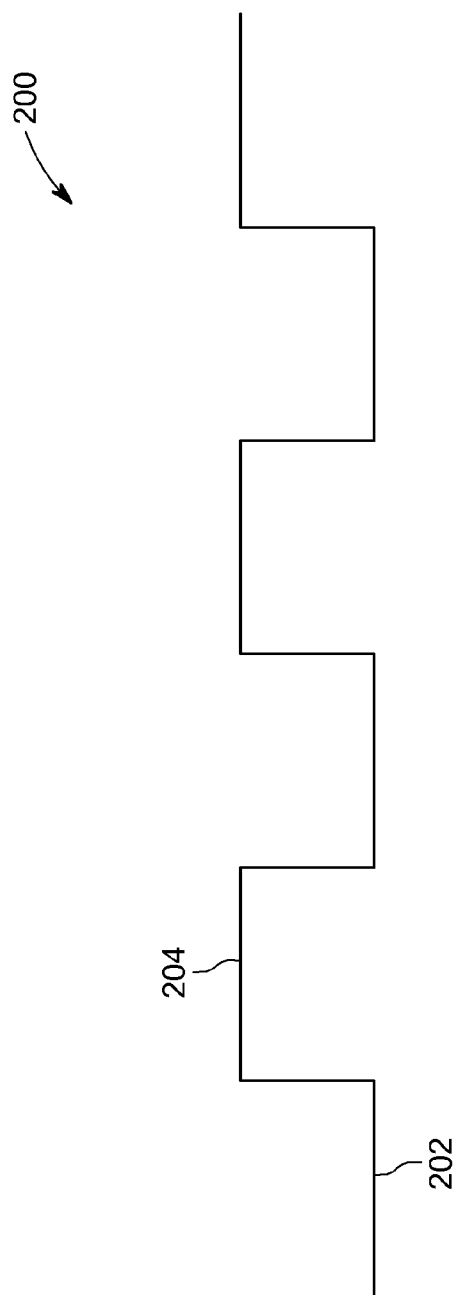
FIG. 3 illustrates an exemplary detector busy signal generated in accordance with various embodiments of the present invention.

At 104, a detector busy signal is acquired from the detector 12. FIG. 3 illustrates an exemplary detector busy signal 200 acquired at 104. The detector busy signal 200 provides an indication that at least one pulse or photon has been detected by the imaging detector 12. For example, during the scanning procedure, when a photon collides with a scintillator on a detector element 20, the absorption of the photon within the detector element 20 produces scintillation photons within the scintillator. In response to the scintillation photons, the detector element 20 produces an analog voltage signal. It should be realized that during the scanning procedure, each detector element indicating a photon collision with a scintillator on the respective detector element 20 generates a respective analog voltage signal. Therefore, the detector busy signal 200 provides an electrical indication to the image reconstruction module 16 that indicates that a specific detector element 20 is busy or currently counting an event or collision. It should also be realized that the detector busy signal 200 does not have to be in the off state 202 for a predetermined or set amount of time. More specifically, the detector busy signal 200 is in the off state 202 only when a photon is not being measured.

Referring again to FIG. 2, at 106, when an event is detected at a detector element 20, the detector busy signal 200 transitions to the on state 204. Specifically, the detector busy signal 200 transitions from the off state 202 to the on state 204. The detector busy signal 200, when operating in the on state 204, indicates that a detector element 20 is currently measuring the energy level of the detected event. In the exemplary embodiment, the energy level of the detected event is measured for a predetermined time, referred to herein as a predetermined time window. The predetermined time window may be between approximately 200 and 500 nanoseconds. For example, when an event is detected at a detector element 20, the total energy of the event is measured for a time period between approximately 200 and 500 nanoseconds. When the predetermined time window has expired, and the total energy of the event has been determined, the detector element 20 is configured to then detect and measure the energy of another subsequent event.

Accordingly, at 108, the detector busy signal 200 then transitions to the off state 202. It should be realized that the steps described at 106-108 are repeated a plurality of times during the scanning procedure. As such, the detector busy signal 200, for each detector element 20, generally includes a plurality of on and off states. The results of the scanning procedure, for example the emission data set and the detector busy signal 200 may be stored as list mode data in the imaging system 10.

Figure 4:
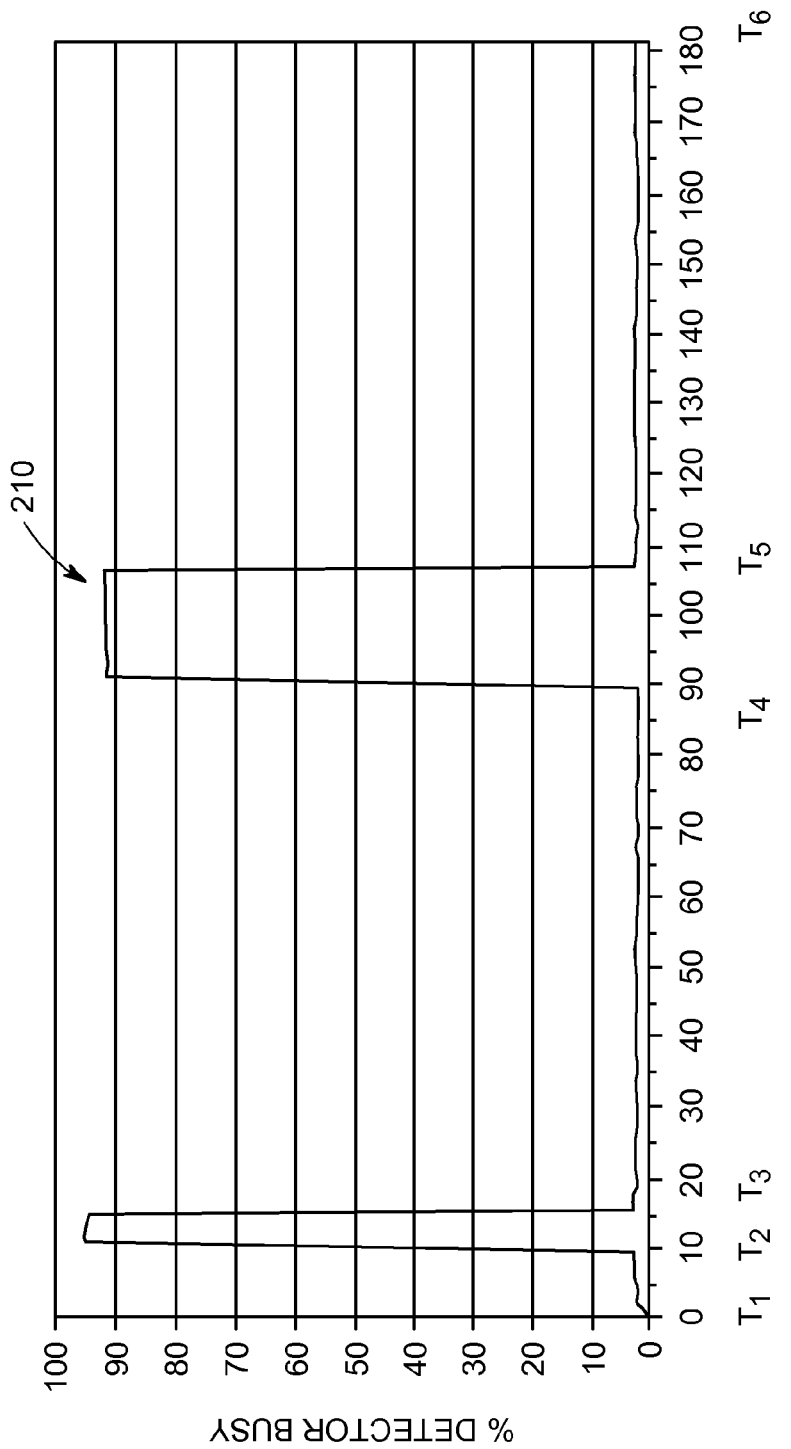
FIG. 4 is a graphical illustration indicating a percentage of time the detector is busy in accordance with various embodiments of the present invention.

At 110, the detector busy signals 200 and the counts received at each detector element 20 are used to identify valid data and invalid data in the image dataset. More specifically, FIG. 4 is a graphical illustration indicating a line 210 that indicates a percentage of time the detector 12 was busy during an exemplary scanning procedure, wherein the x-axis represents the time or duration of an exemplary scan and the y-axis represents the percentage of time the detector was busy during the scan.

For example, time $T_1$ to $T_2$, the percentage of time the detector was indicated as being busy, based on the line 210, is between approximately 0 and 5 percent. In the exemplary embodiment, during the scanning procedure, the detector 12 is expected to be busy somewhere in the range of between approximately 0 percent and 10 percent of the time. In this case, between time $T_1$ to $T_2$, the detector 12 is busy between 0 and 10 percent. As such, the method at 110 may determine that the detector 12 is functioning properly. However, at time $T_2$-$T_3$ and $T_4$-$T_5$, the percentage of time the detector 12 is indicated as being busy is greater than 90 percent. In this case, at 112 the information recorded by the detector 12 between the time periods $T_2$-$T_3$ and $T_4$-$T_5$ may be determined to be invalid data and deleted from the image data set. As a result, in this exemplary embodiment, the image data recorded during the time periods of $T_1$-$T_2$, $T_3$-$T_4$, and $T_5$-$T_6$ is determined to be valid data and forms the subset of image data. It should be realized that data classified as invalid data, $T_2$-$T_3$ and $T_4$-$T_5$, may be data that was acquired when the detector 12 was experiencing a transient failure. It should be realized that image data may be classified as invalid data when actual data was acquired, but based on the analysis performed at 110, the image data was determined to be invalid or erroneous data. The above described method determines when the detector 12 has experienced a transient failure, such as a temporary loss of communication. The location, time, and duration when the detector 12 was not functioning properly and/or was not communicating valid data, and was therefore generating invalid image data, is used to identify and delete the invalid data from the image data set.

In the exemplary embodiment, the image reconstruction module 16 is configured to statistically analyze both the busy signals 200 and the photon counts to identify variations in the image data that are indicative of a component failure. In another embodiment, the image reconstruction module 16 is configured to monitor and assess the integrity of the imaging system 10 and identify when a component, such as a detector element 20 for example, has temporarily failed or a loss of communication has occurred between portions of the imaging system for a portion of the acquisition interval. The invalid data determined at 110 is then removed from the image data set and a subset of image data that includes only valid image data is formed.

At 112, a fractional weight $Wt_i$ is calculated using the subset of valid data. In the exemplary embodiment, the fractional weight $Wt_i$ is calculated based on a fractional time that the detector 12 was determined to be producing valid data. For example, assuming that a duration of an exemplary scan is five minutes and assuming that during the scan the detector 12 was determined to be producing invalid data for thirty seconds, then the invalid data is removed from the image data set to form a subset of valid image data that has a duration of 270 seconds. Thus, during a five minute scan, the detector 12 is producing valid data for 270 seconds and the fractional weight $Wt_i$ is calculated as:

$$Wt_i = \frac{Duration\, of\, ValidData}{Duration\, of\, Scan} = \frac{270\ seconds}{300\ seconds} = 0.9.$$

It should be realized that in the exemplary embodiment, list mode data is used to identify both the valid and invalid data and to calculate the fractional weight $Wt_i$.

Figure 5:
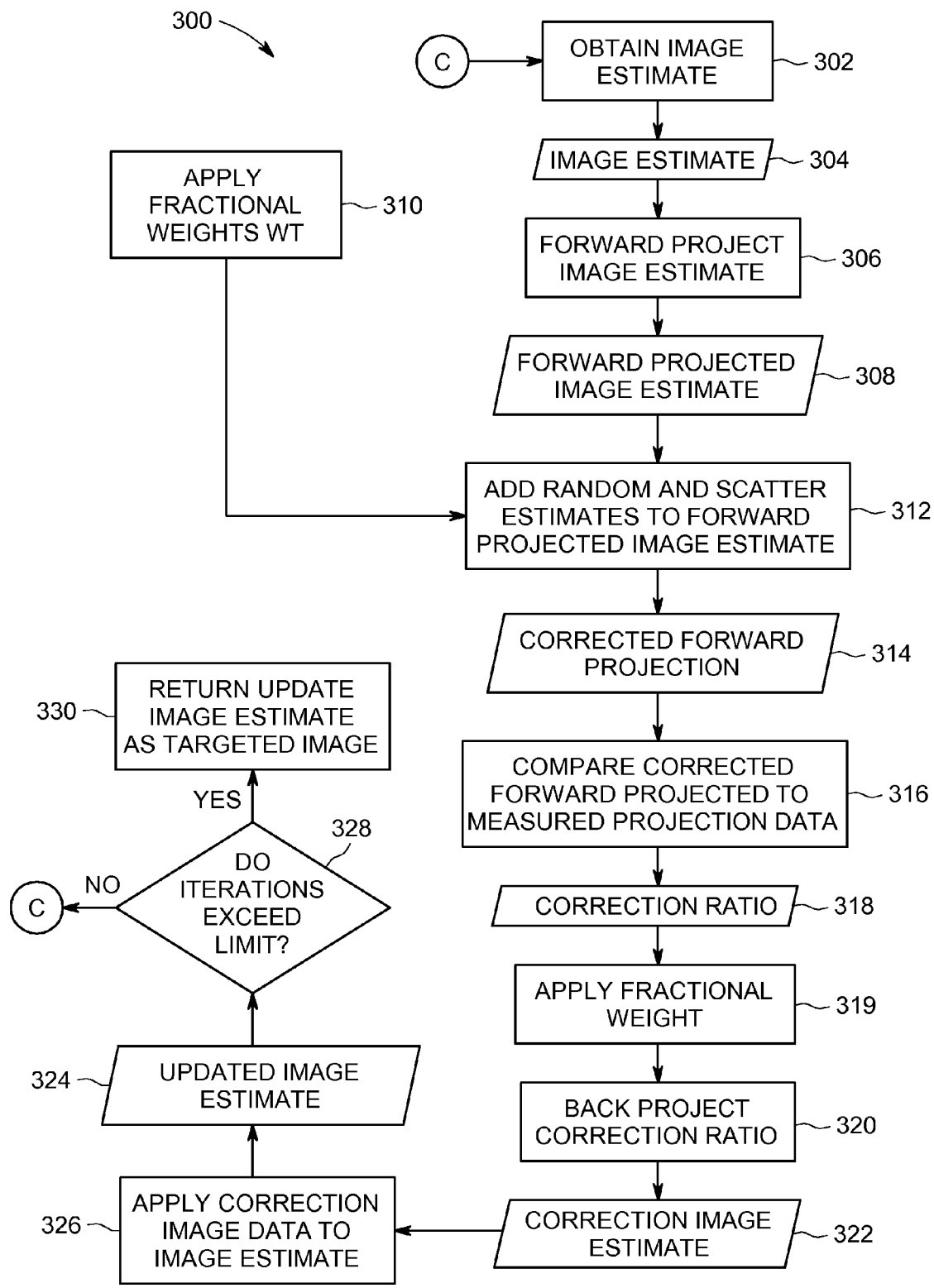
FIG. 5 illustrates an exemplary iterative reconstruction algorithm implemented in accordance with various embodiments of the present invention.

At 114, the fractional weight $Wt_i$ is input into an iterative reconstruction algorithm to reconstruct an image of the object. For example, FIG. 5 is a flowchart 300 illustrating an exemplary iterative algorithm referred to herein as the corrections-in-the-loop technique. In the exemplary embodiment, an image estimate 304 is obtained at 302 for a targeted Field-of-View (FOV) is obtained. The targeted FOV may be selected by the operator and may include only a portion of the object that is being imaged. As will be appreciated, this image estimate 304 may take any of a number of forms and may include a uniform image or an estimate obtained from a reconstruction technique, such as filtered back projection. The image estimate 304 may then be forward projected at 306, to the projection plane to obtain a forward projected image estimate 308. In addition, attenuation factors may also be applied to the forward projected image estimate 308.

At 310 the fractional weights $Wt_i$ calculated at 112 may be then be applied to the forward projected image estimate 308 to generate a corrective term 312. Moreover, random and scatter estimates may also be applied to the forward projected image estimate 308 as part of the corrective term 312 to obtain a corrected forward projection 314. As will be appreciated, the forward projected image estimate 308 may also be corrected for photon scatter, presence of random events, scanner dead time, scanner detector efficiency, scanner geometric effects, and radiopharmaceutical decay.

The corrected forward projection 314 may then be compared to the measured projection data at 316. For example, this comparison may include taking the ratio of the measured projection data and the corrected forward projection acquired 314 to obtain a correction ratio 318. In addition, attenuation factors may be applied to the correction ratio 318. At 319 the fractional weight $Wt_i$ is applied to the correction ratio determined at 318. At 320, the fractionally weighted correction ratio determined at 319 may be back projected to obtain correction image data 322. At 326, the updated estimated image 324 may be acquired by applying the correction image data 322 to the image estimate 304. In one embodiment, the corrected image data 322 and the image estimate 304 are multiplied to obtain the updated image estimate 324 for the targeted FOV. As will be appreciated, the updated image estimate 324 is the image estimate 304 to be used in the next iteration. At 328, it is determined whether the number of iterations for generating the image for the targeted FOV exceeds a threshold value. If the number of iterations exceeds the threshold value, the updated image estimate 324 is returned at 330, as the targeted image. Optionally, rather than using a threshold value, it may be determined whether convergence between the image estimate 304 and the updated image estimate acquired 324 has reached a desired level. Otherwise, the technique of FIG. 5 starting at 302 is performed iteratively.

In the exemplary embodiment, the flowchart 300 shown in FIG. 5 may be implemented utilizing an Ordered Subsets Expectation Maximization (OSEM) algorithm. While the OSEM algorithm is shown below, various embodiments described herein may be implemented using any suitable iterative reconstruction update equation.

Accordingly, the embodiment illustrated by FIG. 5 may be described by equation (1) as follows:

$$\lambda_j^{k,m+1} = \frac{\lambda_j^{k,m}}{\sum_{i \in S_m} P_{i,j} A_i W t_i} \sum_{i \in S_m} P_{i,j} \frac{A_i W t_i y_i}{\sum_j A_i W t_i P_{i,j}, \lambda_j^{k,m} + r_i + s_i} \quad \text{Equation 1}$$

wherein λ refers to an image estimate, $\lambda_j^{k,m}$ refers to the image estimate for pixel j at the $k^{th}$ iteration and the $m^{th}$ of LORs, y refers to the measured projection data for the scan FOV, $y_i$ refers to the measured projection data detected by the $i^{th}$ LOR, i' is the image pixel index;

$r_i$ refers to the estimate of random coincidences detected by the $i^{th}$ LOR, $s_i$ refers to the estimate of scatter coincidences detected by the $i^{th}$ LOR, $A_i$ refers to the attenuation factor along the $i^{th}$ LOR, $Wt_i$ refers to the fractional weight that is applied to the vector $A_i$ based on the identified invalid data, $P_i$ refers to the projection matrix that determines the probability that activity from pixel j is detected by $i^{th}$ LOR, and $S_m$ refers to the $m^{th}$ subset of LORs.

As described above in Equation 1, during the iterative reconstruction process, the $W_t$ represents a fractional "uptime" that is assigned to each LOR. The fractional uptime represents the fractional weight $Wt_i$ that is applied during the iterative reconstruction process shown in FIG. 5. As such, the fractional weight $Wt_i$ is based on the duration or quantity of valid data received from the detector. For example, assuming that 90% of the data received from the detector is classified as valid data, the fractional weight $Wt_i$ applied to the valid data is 0.9. In the exemplary embodiment, the fractional $Wt_i$ is between 0 and 1, wherein 0 indicates that the detector is inoperative during the entire scan and 1 indicates that the detector was operative during the entire duration of the scan. The valid fractionally weighted data is then multiplied by the various factors described above. The various factors include, for example, photon attenuation, system dead-time, and/or detector normalization.

A technical effect of at least some of the various embodiments described herein is to provide methods and an apparatus for performing fault-tolerant reconstruction of an image. The fault-tolerant reconstruction method identifies and compensates for random or transient failures in the imaging system. For example, the fault-tolerant reconstruction method is configured to identify transient failures in the image detector and weight the imaging data based on a duration of the transient failure. A multiplicative corrections array, such as the array P described in Equation 1, is then multiplied by the weights $W_t$ and used in the reconstruction process. Moreover, if the imaging system experiences multiple failed detectors during the scanning procedure, and if there are LORs in the data set connecting two failed detector components, the appropriate weights $W_t$ may be determined from the fraction of time that both components are functioning. Utilizing the fractional weights $Wt_i$ described herein facilitates improving and maintaining image quality when a detector is experiencing a transient failure.

Various embodiments described herein provide a machine-readable medium or media having instructions recorded thereon for a processor or computer to operate an imaging apparatus to perform embodiments of various methods described herein. The medium or media may be any type of CD-ROM, DVD, floppy disk, hard disk, optical disk, flash RAM drive, or other type of computer-readable medium or a combination thereof.

Figure 6:
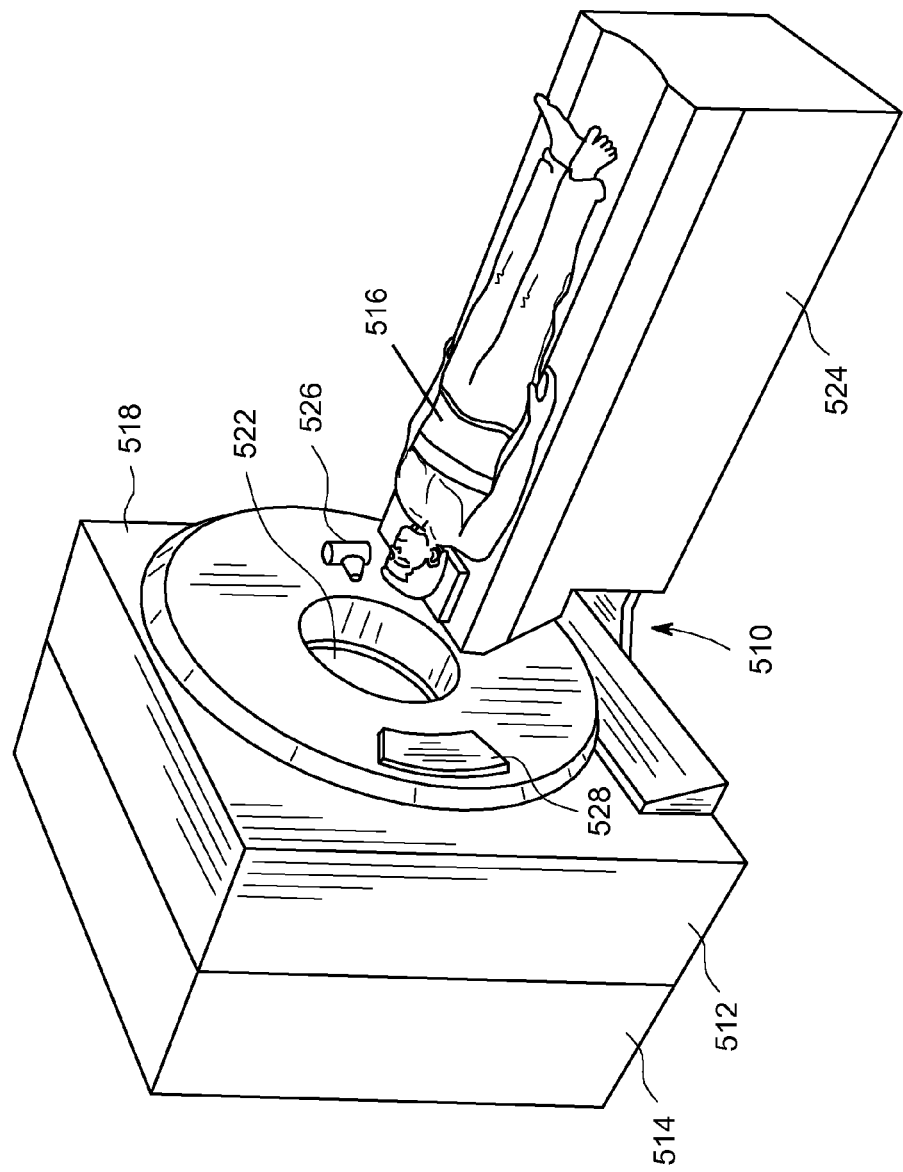
FIG. 6 is a pictorial view of an exemplary multi-modality imaging system formed in accordance with various embodiments of the present invention.

The image reconstruction module 16 may be utilized with an exemplary medical imaging system, such as the imaging system 510 shown in FIGS. 5 and 6. In the exemplary embodiment, the imaging system 510 is a multi-modality imaging system that includes different types of medical imaging systems, such as a Positron Emission Tomography (PET), a Single Photon Emission Computed Tomography (SPECT), a Computed Tomography (CT), an ultrasound system, Magnetic Resonance Imaging (MRI) or any other system capable or generating tomographic images. The image reconstruction module 16 described herein is not limited to multi-modality medical imaging systems, but may be used on a single modality medical imaging system such as a stand-alone PET imaging system or a stand-alone SPECT imaging system, for example. Moreover, the image reconstruction module 16 is not limited to medical imaging systems for imaging human subjects, but may include veterinary or non-medical systems for imaging non-human objects etc.

Referring to FIG. 6, the multi-modality imaging system 510 includes a first modality unit 512 and a second modality unit 514. The two modality units enable the multi-modality imaging system 510 to scan an object or patient, such as an object 516 in a first modality using the first modality unit 512 and to scan the object 516 in a second modality using the second modality unit 514. The multi-modality imaging system 510 allows for multiple scans in different modalities to facilitate an increased diagnostic capability over single modality systems. In one embodiment, first modality unit 512 is a Computed Tomography (CT) imaging system and the second modality 514 is a Positron Emission Tomography (PET) imaging system. The CT/PET system 510 is shown as including a gantry 518. During operation, the object 516 is positioned within a central opening 522, defined through the imaging system 510, using, for example, a motorized table 524. The gantry 518 includes an x-ray source 526 that projects a beam of x-rays toward a detector array 528 on the opposite side of the gantry 518.

Figure 7:
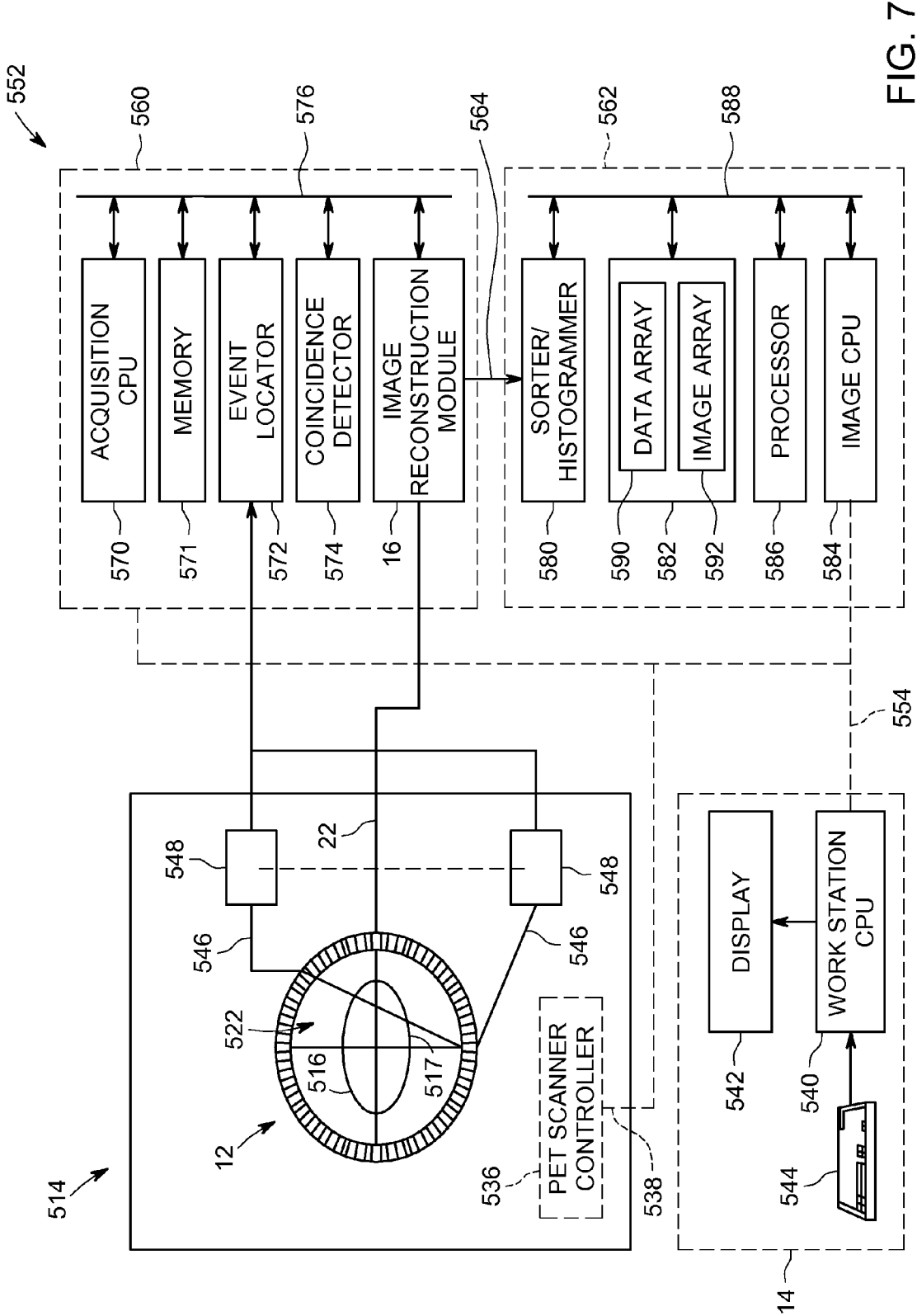
FIG. 7 is a block schematic diagram of the system illustrated in FIG. 6 formed in accordance with various embodiments of the present invention.

FIG. 7 is a detailed block schematic diagram of an exemplary PET imaging system 514 in accordance with an embodiment of the present invention. The PET imaging system 514 includes a detector ring assembly 12 including a plurality of detector scintillators. The detector ring assembly 12 includes the central opening 522, in which an object or patient, such as object 516 may be positioned, using, for example, a motorized table 524 (shown in FIG. 6). The scanning operation is controlled from an operator workstation 14 through a PET scanner controller 536. A communication link 538 may be hardwired between the PET scanner controller 536 and the workstation 14. Optionally, the communication link 538 may be a wireless communication link that enables information to be transmitted to or from the workstation to the PET scanner controller 536 wirelessly. In the exemplary embodiment, the workstation 14 controls real-time operation of the PET imaging system 514. The workstation 14 may also be performed to perform the methods described herein. The operator workstation 14 includes a central processing unit (CPU) or computer 540, a display 542 and an input device 544. As used herein, the term "computer" may include any processor-based or microprocessor-based system configured to execute the methods described herein.

The methods described herein may be implemented as a set of instructions that include various commands that instruct the computer or processor 540 as a processing machine to perform specific operations such as the methods and processes of the various embodiments described herein. For example, the method 100 may be implemented as a set of instructions in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

During operation, when a photon collides with a scintillator on the detector ring assembly 12, a set of acquisition circuits 548 receive these analog signals. The acquisition circuits 548 produce digital signals indicating the 3-dimensional (3D) location and total energy of each event. The acquisition circuits 548 also produce an event detection pulse, which indicates the time or moment the scintillation event occurred. The digital signals are transmitted through a communication link, for example communication link 22 to a data acquisition controller 552 that communicates with the workstation 14 and PET scanner controller 536 via a communication link 554. In one embodiment, the data acquisition controller 552 includes a data acquisition processor 560 and an image reconstruction processor 562 that are interconnected via a communication link 564. During operation, the acquisition circuits 548 transmit the digital signals to the data acquisition processor 560. The data acquisition processor 560 then performs various image enhancing techniques on the digital signals and transmits the enhanced or corrected digital signals to the image reconstruction processor 562 as discussed in more detail below.

In the exemplary embodiment, the data acquisition processor 560 includes at least an acquisition CPU or computer 570. The data acquisition processor 560 also includes an event locator circuit 572 and a coincidence detector 574. The acquisition CPU 570 controls communications on a back-plane bus 576 and on the communication link 564. During operation, the data acquisition processor 560 periodically samples the digital signals produced by the acquisition circuits 548. The digital signals produced by the acquisition circuits 548 are transmitted to the event locator circuit 572. The event locator circuit 572 processes the information to identify each valid event and provide a set of digital numbers or values indicative of the identified event. For example, this information indicates when the event took place and the position of the scintillator that detected the event. Moreover, the event locator circuit may also transmit information to the image reconstruction module 16. The image reconstruction module 16 may then determine whether the detected pulses are valid data or whether gaps in the data are invalid data. Moreover, the image reconstruction module 16 is configured to weight the valid data based on the duration of the valid data. For example, assuming that that 80% of the data received from the detector is classified as valid data, the fractional weight $Wt_i$ applied to the valid data is 0.8. It should be realized that in one exemplary embodiment, the image reconstruction module 16 may be formed as part of the data acquisition controller 552 as shown in FIG. 7. Optionally, the image reconstruction module may be located in the operator workstation 14 as shown in FIG. 1. The events are also counted to form a record of the single channel events recorded by each detector element. An event data packet is communicated to the coincidence detector 574 through the back-plane bus 576.

The coincidence detector 574 receives the event data packets from the event locator circuit 572 and determines if any two of the detected events are in coincidence. Coincident event pairs are located and recorded as a coincidence data packets by the coincidence detector 574 and are communicated through the back-plane bus 576 to the image reconstruction module 16. The output from the coincidence detector 574 is referred to herein as an emission data set or raw image data. In one embodiment, the emission data set may be stored in a memory device 571 that is located in the data acquisition processor 560. Optionally, the emission data set may be stored in the workstation 14. As shown in FIG. 3, the detector busy signal 200 is also transmitted to the image reconstruction module 16.

The weighted image data set, e.g. the image data subset, is then transmitted from the image reconstruction module 16 to a sorter/histogrammer 580 to generate a data structure known as a histogram. Optionally, the image reconstruction module 16 may generate the histograms described herein. The image reconstruction processor 562 also includes a memory module 582, an image CPU 584, an array processor 586, and a communication bus 588. During operation, the sorter/histogrammer 580 performs motion related histogramming described above to generate the events listed in the image data subset into 3D data. This 3D data, or sinograms, is organized in one exemplary embodiment as a data array 590. The data array 590 is stored in the memory module 582. The communication bus 588 is linked to the communication link 554 through the image CPU 584. The image CPU 584 controls communication through communication bus 588. The array processor 586 is also connected to the communication bus 588. The array processor 586 receives the data array 590 as an input and reconstructs images in the form of image arrays 592. Resulting image arrays 592 are then stored in the memory module 582. The images stored in the image array 592 are communicated by the image CPU 584 to the operator workstation 14.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. For example, the ordering of steps recited in a method need not be performed in a particular order unless explicitly stated or implicitly required (e.g., one step requires the results or a product of a previous step to be available). Many other embodiments will be apparent to those of skill in the art upon reviewing and understanding the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for reconstructing an image of an object, said method comprising:
   acquiring an image dataset of an object of interest;
   identifying valid data and invalid data in the image dataset;
   determining a time period that includes the valid data;
   weighting the valid data based on the determined time period; and
   reconstructing an image of the object using the weighted valid data.

2. A method in accordance with claim 1 wherein the acquiring further comprises:
   acquiring a list mode image dataset of the object of interest; and
   determining a fractional time period a detector experienced a transient failure based on the invalid data.

3. A method in accordance with claim 1 further comprising iteratively reconstructing an image of the object using the weighted valid data.

4. A method in accordance with claim 1 further comprising weighting the valid data using a fractional weight that is between 0 and 1.

5. A method in accordance with claim 1 further comprising weighting the valid data using a fractional weight that is determined by dividing a duration of valid data by a duration of the scanning procedure.

6. A method in accordance with claim 1 further comprising determining a fractional time a detector experienced a transient failure using a detector busy signal.

7. A method in accordance with claim 1 further comprising weighting a plurality of lines of response (LOR) using a fractional weight.

8. A method in accordance with claim 1 wherein the reconstructing further comprises applying a fractional weight to a forward projected image estimate during an iterative reconstruction process.

9. A medical imaging system comprising a detector and an image reconstruction module coupled to the detector, wherein the image reconstruction module is programmed to:
   receive an image dataset of an object of interest;
   identify valid data and invalid data in the image dataset;
   determine a fractional time a detector experienced a transient failure based on the invalid data;
   weight the valid data based on the fractional time; and
   reconstruct an image of the object using the weighted valid data.

10. A medical imaging system in accordance with claim 9, wherein the image reconstruction module is further programmed to iteratively reconstruct an image of the object using the weighted valid data.

11. A medical imaging system in accordance with claim 9, wherein the image reconstruction module is further programmed to weight the valid data using a fractional weight that is between 0 and 1.

12. A medical imaging system in accordance with claim 9, wherein the image reconstruction module is further programmed to weight the valid data using a fractional weight that is determined by dividing a duration of valid data by a duration of the scanning procedure.

13. A medical imaging system in accordance with claim 9, wherein the image reconstruction module is further programmed to:
   receive a detector busy signal; and
   determine a fractional time a detector experienced a transient failure using the detector busy signal.

14. A medical imaging system in accordance with claim 9, wherein the image reconstruction module is further programmed to weight each line of response (LOR) using a fractional weight.

15. A medical imaging system in accordance with claim 9, wherein the image reconstruction module is further programmed to apply a fractional weight to a forward projected image estimate during an iterative reconstruction process.

16. A non-transitory computer readable medium encoded with a program to instruct a computer to:
   receive an image dataset of an object of interest;
   identify valid data and invalid data in the image dataset;
   determine a fractional time a detector experienced a transient failure based on the invalid data;

weight the valid data based on the fractional time; and
reconstruct an image of the object using the weighted valid data.

17. A non-transitory computer readable medium in accordance with claim 16 wherein the program further instructs a computer to iteratively reconstruct an image of the object using the weighted valid data.

18. A non-transitory computer readable medium in accordance with claim 16 wherein the program further instructs a computer to weight the valid data using a fractional weight that is between 0 and 1.

19. A non-transitory computer readable medium in accordance with claim 16 wherein the program further instructs a computer to weight the valid data using a fractional weight that is determined by dividing a duration of valid data by a duration of the scanning procedure.

20. A non-transitory computer readable medium in accordance with claim 16 wherein the program further instructs a computer to determine a fractional time a detector experienced a transient failure using a detector busy signal.

* * * * *